United States Patent
Tashiro et al.

(10) Patent No.: US 8,299,223 B2
(45) Date of Patent: Oct. 30, 2012

(54) PSEUDOGLYCOLIPID AND USE THEREOF

(75) Inventors: Takuya Tashiro, Kanagawa (JP); Kenji Mori, Kanagawa (JP); Ken-ichi Fuhshuku, Kanagawa (JP); Masaru Taniguchi, Kanagawa (JP); Ryusuke Nakagawa, Kanagawa (JP); Hiroshi Watarai, Kanagawa (JP)

(73) Assignee: Riken, Wako-shi (JP)

( * ) Notice: Subject to any disclaimer, the term of this patent is extended or adjusted under 35 U.S.C. 154(b) by 220 days.

(21) Appl. No.: 12/528,232

(22) PCT Filed: Feb. 22, 2008

(86) PCT No.: PCT/JP2008/053105
§ 371 (c)(1),
(2), (4) Date: Nov. 23, 2009

(87) PCT Pub. No.: WO2008/102888
PCT Pub. Date: Aug. 28, 2008

(65) Prior Publication Data
US 2010/0062990 A1    Mar. 11, 2010

(30) Foreign Application Priority Data
Feb. 22, 2007 (JP) ................ 2007-042873

(51) Int. Cl.
*C07H 17/02* (2006.01)
(52) U.S. Cl. ..................................... 536/17.9
(58) Field of Classification Search ............ 536/17.9
See application file for complete search history.

(56) References Cited

U.S. PATENT DOCUMENTS

2002/0032158 A1    3/2002    Tomiyama et al.
2005/0222048 A1    10/2005   Tsuji et al.

FOREIGN PATENT DOCUMENTS

DE          101 28 250 A1    12/2001
WO          WO 03/105769 A2  12/2003
WO          WO 2007/050668 A1 5/2007

OTHER PUBLICATIONS

Tashiro et al, Tetrahedron Letters 48 (2007) 3343-3347.*
Thornber, C. W., Chem. Soc. Rev., 1979, 8, 563-580.*
Schmieg et al., *J. Exp. Med.*, 198 (11): 1631-1641 (Dec. 1, 2003).
Tsunoda et al., *Liebigs Anna.*, 1995 (2): 267-277 (1995).
Yang et al., *Angew. Chem. Int. Ed.*, 43: 3818-3822 (2004).

* cited by examiner

*Primary Examiner* — Eric S Olson
*Assistant Examiner* — Zhengfu Wang
(74) *Attorney, Agent, or Firm* — Leydig, Voit & Mayer, Ltd.

(57) ABSTRACT

The invention provides a pseudoglycolipid effective for cancer treatment and the like and a novel synthesis intermediate therefor, as well as a medicament containing the pseudoglycolipid and the like. The inventive compound is represented by the formula (1), or a salt thereof,

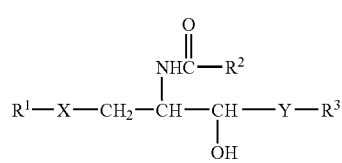

(1)

wherein each symbol is as defined in the specification.

6 Claims, 4 Drawing Sheets

PSEUDOGLYCOLIPID AND USE THEREOF

CROSS-REFERENCE TO RELATED APPLICATION(S)

This application is the U.S. national stage of International Patent Application No. PCT/JP2008/053105, filed on Feb. 22, 2008, which claims priority to Japan Patent Application No. 2007-042873 filed on Feb. 22, 2007.

TECHNICAL FIELD

The present invention relates to a novel pseudoglycolipid and use thereof. More particularly, the present invention relates to a novel pseudoglycolipid having, in the skeleton, a carbasugar wherein a ring oxygen atom of the sugar is replaced with a methylene group, and a pharmaceutical use thereof.

BACKGROUND ART

Immune systems of living organisms have an elaborate surveillance function to distinguish normal cells and abnormal cells in the body of themselves, and remove only the abnormal cells. However, when the surveillance function collapses, abnormal cells produced by mutation and the like cannot be removed but proliferate in the body. A mass of such proliferated abnormal cells is a tumor, i.e., cancer.

Cancer is mainly treated by surgical removal of cancer or use of anti-cancer agents. However, these treatment methods place physical burden due to removal surgery or side effects of anti-cancer agents, as well as mental burden due to operative scar.

In such background, a treatment method using an immunotherapy in combination is drawing attention. In the immunotherapy, cancer cells are attacked by increasing the number of immunocytes in patients themselves, and activating them. If the size of tumor formed by cancer cells can be reduced, the physical burden due to the removal surgery becomes small. In addition, since the operative scar is small, the mental burden is drastically reduced.

Natural killer (NK) T cells are immunocytes belonging to a novel lymphocyte lineage showing characteristics different from those of other lymphocyte lineages (T, B, NK cells). Since cytotoxic perforin granules are present in NKT cells, they are analogous to NK cells (non-patent document 1). However, since NKT cells express not only NK cell marker but also T cell receptor (TCR), it is clear that they form a definitively different, new cell group (non-patent document 2). NKT cells can produce both Th-1 type cytokine (mainly interferon (IFN)-γ produced by helper T (Th)-1 cell that promotes immunostimulatory action and Th-2 type cytokine (mainly interleukin (IL)-4) produced by Th-2 cell that promotes immunosuppressive action (non-patent document 3), which suggests a possibility of controlling the balance of immune system (non-patent document 4). Therefore, by controlling the function of NKT cells, disrupted balance of the immune system is controlled and the surveillance function is enhanced, whereby cancer can be treated.

The most noticeable characteristic of NKT cells is that the α chain of TCR expressed by NKT cells is common to all members of one species. In other words, this means that all NKT cells of the living organisms belonging to the same species are activated by the same substance. This α chain is Vα24 in human and Vα14 in mouse, and they show extremely high homology between the two species. In addition, only very limited kinds of β chain are known to form a pair with the α chain. For this reason, this TCR is also called a "non-variable TCR".

There are various kinds of glycosphingolipids which are known to be present in the body. In glycosphingolipids in the body, various sugars generally form a β-bond with ceramide. While the existent amount thereof varies depending on the organ, they are present in the cellular membrane of various organs (non-patent document 5).

In the meantime, a report has recently been documented that glycosphingolipids wherein sugar forms an α-bond with ceramide has a strong immunostimulatory action and an anti-tumor activity. α-Galactosylceramide represented by Agelasphins is a glycolipid isolated from an extract of *Agelas mauritianus*, one kind of sponge, and is known to strongly activate NKT cells (non-patent document 6).

After intake by antigen presenting cell (APC), which is represented by dendritic cell (DC) and the like, α-galactosylceramide is presented on the cellular membrane by a CD1d protein similar to major histocompatible complex (MHC) class I molecule. NKT cells are activated by recognition using TCR of the thus-presented complex of CD1d protein and α-galactosylceramide, which triggers various immune reactions.

α-Galactosylceramide is glycosphingolipids wherein galactose is bonded by α-configuration to a ceramide formed by acylation of sphingosine base with long chain fatty acid. Various analogs have been synthesized heretofore, and the correlation between structures and activities thereof has been investigated. It has been clarified that, in a series of synthesis analogs, for example, α-galactosylceramide represented by the following formula (a) (hereinafter to be referred to as "α-GalCer") shows the strongest activity, and further, that the corresponding β-configuration (β-GalCer) does not show an immunostimulatory activity (non-patent document 7).

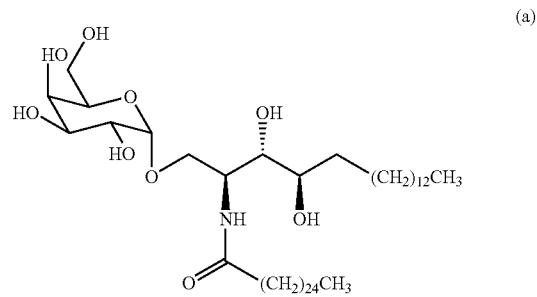

(a)

In recent years, therapeutic drugs containing α-GalCer as an active ingredient have been proposed or developed, taking note of such function of NKT cells. However, NKT cells activated by the administration of α-GalCer simultaneously produce, along with the production of IFN-γ, which is a cytokine that induces an immunostimulatory activity and is useful for cancer treatment, IL-4, which is a cytokine that induces an immunosuppressive action, and IL-10, which is a cytokine that induces an immunity regulating action. As a result, problems occur since immunostimulatory activity is suppressed and a sufficient effect for cancer treatment is difficult to provide.

In recent years, a glycolipid (α-C-GalCer) that preferentially produces IFN-γ, which is a cytokine that induces an immunostimulatory action of NKT cell, has been developed (patent documents 1-3, non-patent document 8). α-C-GalCer is an analog wherein the oxygen atom forming a glucoside bond of α-GalCer is substituted by a methylene group. It has been reported that the in vivo stability is enhanced and the efficacy is maintained for a long time since, in α-C-GalCer, the bond between sugar and ceramide is converted from a glycoside bond to a carbon-carbon bond (non-patent document 9). However, the reason for preferential production of IFN-γ by α-C-GalCer has not been elucidated yet. In addition, the IFN-γ/IL-4 ratio is not entirely sufficient from the clinical aspects and further improvement is desired.

patent document 1: US-A-2005/0222048
patent document 2: WO2003/105769
patent document 3: DE-A-10128250
non-patent document 1: Proc. Natl. Acad. Sci. USA 1998, 95, 5690-5693
non-patent document 2: J. Immunol. 1995, 155, 2972-2983
non-patent document 3: J. Immunol. 1998, 161, 3271-3281
non-patent document 4: Nat. Immunol. 2003, 4, 1164-1165
non-patent document 5: Biochim. Biophys. Acta 1973, 315-335
non-patent document 6: Science 1997, 278, 1626-1629
non-patent document 7: J. Med. Chem. 1995, 38, 2176-2187
non-patent document 8: Angew. Chem. Int. Ed. Engl. 2004, 43, 3818-3822
non-patent document 9: J. Exp. Med. 2003, 198, 1631-1641

DISCLOSURE OF THE INVENTION

Problems to be Solved by the Invention

The present invention has been made in view of such situation, and its problem to be solved is provision of a novel pseudoglycolipid effective for cancer treatment and an intermediate useful for synthesizing the pseudoglycolipid. The present invention also aims to provide a medicament such as an anti-cancer agent containing the novel pseudoglycolipid and the like.

Means of Solving the Problems

The present inventors have conducted intensive studies in an attempt to solve the above-mentioned problems, and found that a pseudoglycolipid having, in the skeleton, a carbasugar wherein a pyranose ring oxygen atom is replaced with a methylene group selectively produces a particular cytokine. The present inventors have further studied in detail, and found that a specific immunostimulatory activity is expressed by the selective production of the particular cytokine, which is extremely effective for cancer treatment, which resulted in the completion of the present invention.

Accordingly, the present invention provides the following.

[1] A compound represented by the following formula (1)

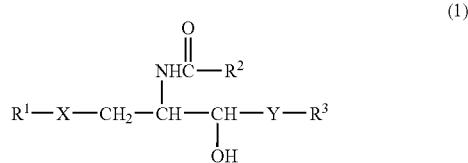

wherein $R^1$ is an α-carbasugar residue, $R^2$ and $R^3$ are each independently a substituted or unsubstituted hydrocarbon group having a carbon number of 1 to 28, X is an oxygen atom, a sulfur atom, —$CH_2$— or —NH—, and Y is —$CH_2$—, —CH(OH)— or —CH=CH— (hereinafter to be referred to as "compound (1)"), or a salt thereof.

[2] The compound of the above-mentioned [1], wherein $R^1$ is a 5a-carba-α-D-galactopyranosyl group, or a salt thereof.
[3] The compound of the above-mentioned [1], wherein $R^1$ is a 5a-carba-α-D-fucopyranosyl group, or a salt thereof.
[4] The compound of any of the above-mentioned [1] to [3], wherein $R^2$ is a substituted or unsubstituted alkyl group having a carbon number of 1 to 28, or a salt thereof.
[5] The compound of any of the above-mentioned [1] to [4], wherein $R^3$ is a substituted or unsubstituted alkyl group having a carbon number of 1 to 28, or a salt thereof.
[6] The compound of any of the above-mentioned [1] to [5], wherein X is an oxygen atom, or a salt thereof.
[7] The compound of any of the above-mentioned [1] to [6], wherein Y is —CH(OH)—, or a salt thereof.
[8] A compound represented by the following formula (2)

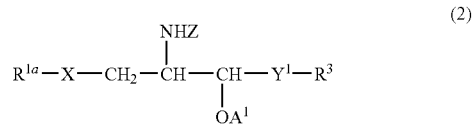

wherein $R^{1a}$ is an α-carbasugar residue wherein a hydroxyl group is protected, $R^3$ is a substituted or unsubstituted hydrocarbon group having a carbon number of 1 to 28, X is an oxygen atom, a sulfur atom, —$CH_2$— or —NH—, $Y^1$ is —$CH_2$—, —CH($OA^1$)- or —CH=CH—, Z is an amino-protecting group, and $A^1$ is a hydrogen atom or a hydroxyl-protecting group, provided that when $Y^1$ is —CH($OA^1$)-, two $A^1$ in combination optionally form a protecting group (hereinafter to be referred to as "compound (2)"), or a salt thereof.
[9] A medicament comprising compound (1) or a salt thereof.
[10] An immunostimulator comprising compound (1) or a salt thereof.
[11] A selective IFN-γ production inducer comprising compound (1) or a salt thereof.
[12] An anti-cancer agent comprising compound (1) or a salt thereof.
[13] A method for immunostimulation, comprising administering an effective amount of compound (1) or a salt thereof to a subject.
[14] A method for inducing selective IFN-γ production, comprising administering an effective amount of compound (1) or a salt thereof to a subject.
[15] A method for treating cancer, comprising administering an effective amount of compound (1) or a salt thereof to a subject.
[16] Use of compound (1) or a salt thereof for the production of an immunostimulator.
[17] Use of compound (1) or a salt thereof for the production of a selective IFN-γ production inducer.
[18] Use of compound (1) or a salt thereof for the production of an anti-cancer agent.
[19] A commercial package comprising a composition comprising compound (1) or a salt thereof, and a written matter describing that the composition can or should be used for immunostimulation, selective IFN-γ production induction or cancer treatment.

Effect of the Invention

When compound (1) or a salt thereof of the present invention forms a complex with the CD1d protein possessed by APC and the complex is presented to NKT cells, the NKT cells recognizes the complex via TCR, and can selectively produce IFN-γ, which is one kind of cytokine that activates the function of immunocytes, in a large amount, from among the immunoregulatory functions it has. As a result, an immunostimulatory action is promoted and significant attack on the abnormal cells has become possible.

In addition, since compound (1) or a salt thereof of the present invention has extremely enhanced stability in the body as compared to α-GalCer, and can strongly activate NKT cells even by the administration of a small amount thereof, it can enhance IFN-γ producibility as compared to conventionally known glycolipids.

Therefore, compound (1) or a salt thereof of the present invention is extremely useful for cancer treatment and effective since it does not cause any particularly noticeable side effects. Consequently, it can reduce physical and mental burdens on patients caused by conventional removal surgery of cancer and the like. In addition, it can also be used as a reagent for biological test and study.

Compound (2) or a salt thereof of the present invention is useful as a synthesis intermediate for compound (1) or a salt thereof.

BEST MODE FOR CARRYING OUT THE INVENTION

Figure 1:
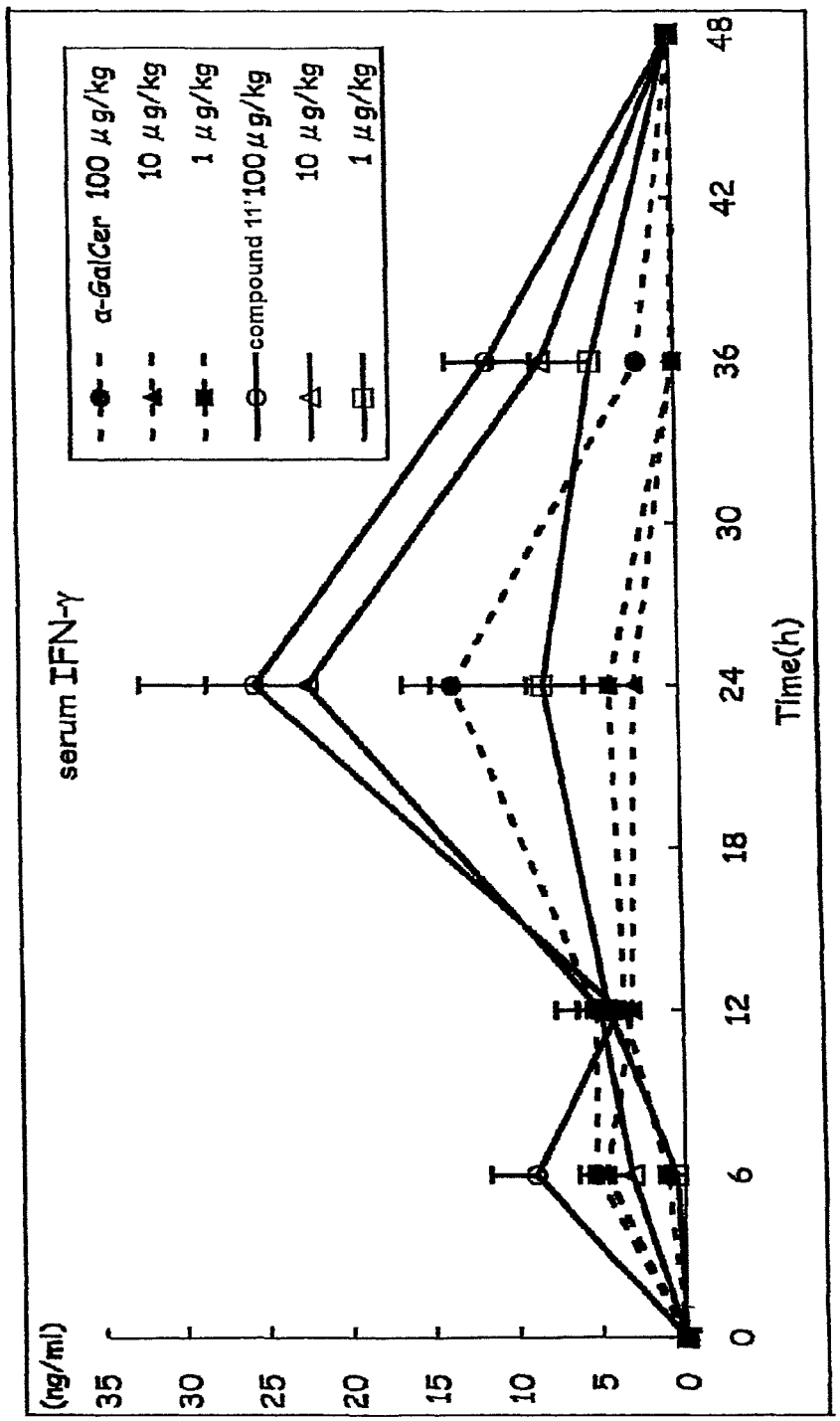
FIG. 1 shows the measurement results of IFN-γ production amount in Experimental Example 1. In the figure, μg/kg shows μg/kg body weight.

The present invention is explained in detail in the following by referring to a preferable embodiment thereof.

At first, the definitions of the symbols used in the formulas in the present specification are explained.

$R^1$ is an α-carbasugar residue, $R^{1a}$ is an α-carbasugar residue wherein a hydroxyl group is protected. In the α-carbasugar residue for $R^{1a}$, all hydroxyl groups are generally protected. Here, the "carbasugar residue" is a residue obtained by removing a reducing terminal hydroxyl group from a pseudocarbohydrate wherein the ring oxygen atom of sugar is replaced with a methylene group.

Preferable examples of the carbasugar residue include 5a-carba-α-D-galactopyranosyl, 5a-carba-α-D-glucopyranosyl and 5a-carba-α-D-fucopyranosyl.

Examples of the hydroxyl-protecting group for the carbasugar residue include an acyl group, a t-butyldimethylsilyl (TBS) group, a trimethylsilyl (TMS) group, a benzyl (Bn) group, a p-methoxybenzyl (PMB) group and the like. Of these, a Bn group and a PMB group are preferable.

The "acyl group" in the present specification is, for example, a formyl group; an alkyl-carbonyl group (e.g., an alkyl-carbonyl group (e.g., acetyl group, propionyl group, butyryl group, isobutyryl group, valeryl group, pivaloyl group, hexanoyl group) wherein the alkyl moiety is a straight chain or branched alkyl group having a carbon number of 1 to 24 (preferably 1 to 12)); a cycloalkyl-carbonyl group (e.g., a cycloalkyl-carbonyl group wherein the cycloalkyl moiety is a cycloalkyl group having a carbon number of 3 to 10); an alkenyl-carbonyl group (e.g., an alkenyl-carbonyl group (e.g., acryloyl group, methacryloyl group) wherein the alkenyl moiety is a straight chain or branched alkenyl group having a carbon number of 2 to 12); an aryl-carbonyl group (e.g., an aryl-carbonyl group (e.g., benzoyl group, naphthoyl group) wherein the aryl moiety is an aryl group having a carbon number of 6 to 14) and the like. The aryl group of the aryl-carbonyl group is, for example, a monocyclic-tricyclic aromatic hydrocarbon group, and specific examples include a phenyl group, a naphthyl group, an anthryl group and a phenanthryl group. Of these, as the acyl group, a formyl group, an acetyl group, a propionyl group, a butyryl group, an isobutyryl group, a benzoyl group, a naphthoyl group and the like are preferable, and an acetyl group and a benzoyl group are more preferable.

$R^2$ and $R^3$ are each independent a substituted or unsubstituted hydrocarbon group having a carbon number of 1 to 28. The "hydrocarbon group" in the present specification is a concept encompassing a substituted or unsubstituted alkyl group having a carbon number of 1 to 28, an alkenyl group having a carbon number of 2 to 28, an alkynyl group having a carbon number of 2 to 28, a cycloalkyl group having a carbon number of 3 to 28, a cycloalkenyl group having a carbon number of 3 to 28, and an aryl group having a carbon number of 6 to 14, which may be in any of linear, branched and cyclic forms. In addition, $R^2$ and $R^3$ may be a saturated hydrocarbon group or an unsaturated hydrocarbon group, and may have an unsaturated bond in a molecule or at any terminal. Of these, as $R^2$ and $R^3$, a substituted or unsubstituted alkyl group having a carbon number of 1 to 28 is preferable.

Examples of the substituent of the hydrocarbon group for $R^2$ or $R^3$ include an electron-donating group such as halogen (preferably chlorine atom, fluorine atom); an alkoxy group (preferable carbon number 1-24, more preferable carbon number 1-16, still more preferable carbon number 1-10, particularly preferable carbon number 1-4) such as a methoxy group, an ethoxy group, a propoxy group, an isopropoxy group, a butoxy group, a tert-butoxy group and the like; an aryloxy group (preferable carbon number 6-14) such as a phenoxy group and the like; a hydroxyl group; an amino group; an alkylamino group such as a methylamino group, a dimethylamino group, an ethylamino group, a diethylamino group and the like; a cycloalkylamino group; an alkylcarbonylamino group such as an acetamide group and the like; a cycloalkylcarbonylamino group; an arylcarbonylamino group (preferably, an arylcarbonylamino group wherein the aryl moiety is an aryl group having a carbon number of 6 to 14) such as a benzoylamino group etc. and the like, and further an electron-withdrawing group such as a carboxyl group; an alkoxycarbonyl group; and an acyl group (which is as mentioned above. Preferably, an alkyl-carbonyl group wherein the alkyl moiety is a straight chain or branched alkyl group having a carbon number of 1 to 24); a carbamoyl group; a trifluoromethyl group and the like.

Examples of the alkyl moiety of the above-mentioned alkylamino group and alkylcarbonylamino group include a straight chain or branched alkyl group (preferable carbon number 1-24, more preferable carbon number 1-16, still more preferable carbon number 1-10, particularly preferable carbon number 1-4) such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group and the like.

Examples of the cycloalkyl moiety of the above-mentioned cycloalkylamino group and cycloalkylcarbonylamino group include a cycloalkyl group (preferable carbon number 3-24, more preferable carbon number 3-16, still more preferable carbon number 3-10, particularly preferable carbon number 3-6) such as a cyclopentyl group, a cyclohexyl group and the like.

Examples of the alkoxy moiety of the above-mentioned alkoxycarbonyl group include those similar to the above-mentioned alkoxy group.

The above-mentioned substituents may be further substituted at substitutable position(s) by at least one kind from halogen, an alkyl group, a cycloalkyl group, an alkenyl group, an alkynyl group, a phenyl group, an alkoxy group, a hydroxyl group, an amino group, an alkylamino group and a cycloalkylamino group.

Examples of the halogen, alkoxy group, alkylamino group and cycloalkylamino group include those similar to the above.

Examples of the alkyl group include an alkyl group (preferable carbon number 1-24, more preferable carbon number 1-16, still more preferable carbon number 1-10, particularly preferable carbon number 1-4) such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group and the like.

Examples of the cycloalkyl group include a cycloalkyl group (preferable carbon number 3-24, more preferable carbon number 3-16, still more preferable carbon number 3-10, particularly preferable carbon number 3-6) such as a cyclopentyl group, a cyclohexyl group and the like.

Examples of the alkenyl group include an alkenyl group (preferable carbon number 2-24, more preferable carbon number 2-16, still more preferable carbon number 2-10, particularly preferable carbon number 2-4) such as a vinyl group, a propenyl group, a butenyl group and the like.

Examples of the alkynyl group include an alkynyl group (preferable carbon number 2-24, more preferable carbon number 2-16, still more preferable carbon number 2-10, particularly preferable carbon number 2-4) such as an ethynyl group, a propargyl group, a butynyl group, a pentynyl group and the like.

Of these, as $R^2$, a substituted or unsubstituted alkyl group is preferable, and the carbon number thereof is preferably 18-26, more preferably 24-26. In addition, as $R^2$, a linear alkyl group is preferable. Specific examples of $R^2$ include —$(CH_2)_{23}$—$CH_3$, —$(CH_2)_{24}$—$CH_3$, —$(CH_2)_{25}$—$CH_3$ and the like.

In addition, as $R^3$, a substituted or unsubstituted alkyl group is preferable, and the carbon number thereof is preferably 9-20, more preferably 12-18. In addition, as $R^3$, a linear alkyl group is preferable. Specific examples of $R^3$ include —$(CH_2)_{11}$—$CH_3$, —$(CH_2)_{12}$—$CH_3$, —$(CH_2)_{13}$—$CH_3$, —$(CH_2)_{14}$—$CH_3$, —$(CH_2)_{15}$—$CH_3$, —$(CH_2)_{16}$—$CH_3$, —$(CH_2)_{17}$—$CH_3$ and the like.

X is an oxygen atom, a sulfur atom, —$CH_2$— or —NH—. Of these, an oxygen atom, a sulfur atom or —NH— is preferable, and an oxygen atom is more preferable.

Y is —$CH_2$—, —CH(OH)— or —CH=CH—. Of these, —CH(OH)— is preferable.

$Y^1$ is —$CH_2$—, —$CH(OA^1)$- or —CH=CH—. Of these, —$CH(OA^1)$- is preferable. $A^1$ is as mentioned below.

$A^1$ is a hydrogen atom or a hydroxyl-protecting group. Examples of the hydroxyl-protecting group include an acyl group, a TBS group, a Bn group, a PMB group and the like.

The acyl group is as mentioned above. Of these, a TBS group and a Bn group are preferable.

When $Y^1$ is —$CH(OA^1)$-, two $A^1$ may be the same or different; however, they are preferably the same.

When $Y^1$ is —$CH(OA^1)$-, two $A^1$ in combination may form a protecting group for diol. Examples of the diol-protecting group include a group represented by

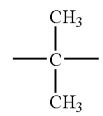

(that is, a group that protects diol and forms acetonide) and the like.

Z is an amino-protecting group. Examples thereof include an acyl group, a TBS group, a Bn group, a PMB group, a 9-fluorenylmethoxycarbonyl (Fmoc) group, a benzyloxycarbonyl (Cbz) group, a tosyl group and the like. The acyl group is as mentioned above. Of these, a Bn group and a PMB group are preferable.

In the present invention, the α configuration is employed from among the stereoisomers derived from the cyclic structure of carbasugar. The present inventors have found that the β configuration shows extremely lower cytokine-producing ability.

When compound (1) and compound (2) have stereoisomers, any isomers are also encompassed in the present invention, which may be a mixture (including racemate) of two or more kinds of isomers at any ratio.

Particularly, compound (1) contains at least 4 optical isomers derived from asymmetric carbon in the lipid moiety. In the present invention, they may be a single optically active form or a mixture (including racemate) of two or more kinds of optically active forms at any ratio. The asymmetric carbon to be bonded to —$NHCOR^2$ is preferably an S configuration. The asymmetric carbon having —OH and adjacent to the asymmetric carbon to be bonded to —$NHCOR^2$ is preferably an anti configuration relative to the asymmetric carbon to be bonded to —$NHCOR^2$. When Y is —CH(OH)—, the asymmetric carbon in —CH(OH)— for Y is preferably an R configuration.

In addition, compound (2) contains an optical isomer derived from asymmetric carbon in the lipid moiety. In the present invention, it may be a single optically active form or a mixture (including racemate) of two or more kinds of optically active forms at any ratio. The asymmetric carbon to be bonded to —NHZ is preferably an S configuration. The asymmetric carbon having —$OA^1$ and adjacent to the asymmetric carbon to be bonded to —NHZ is preferably an anti configuration relative to the asymmetric carbon to be bonded to —NHZ. When $Y^1$ is —$CH(OA^1)$-, the asymmetric carbon in —$CH(OA^1)$- for $Y^1$ is preferably an R configuration.

Examples of compound (1) include

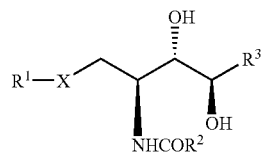

wherein each symbol is as defined above, and the like.

Examples of compound (2) include

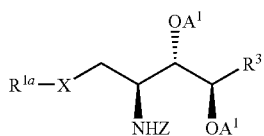

wherein each symbol is as defined above, and the like.

The salts of compound (1) and compound (2) are preferably pharmacologically acceptable salts. Examples thereof include inorganic acid salts such as hydrochloride, hydrobromide, hydroiodide, sulfate, nitrate, phosphate and the like; organic acid salts such as succinate, fumarate, acetate, methanesulfonate, toluenesulfonate and the like; alkali metal salts such as sodium salt, potassium salt and the like; alkaline earth metal salts such as magnesium salt, calcium salt and the like; ammonium salts such as ammonium salt, alkylammonium salt etc. and the like.

Specific preferable examples of compound (1) in the present invention are shown in, but are not limited to, Tables 1-5.

TABLE 1

| compound No. | $R^1$ | X | $R^2$ | Y | $R^3$ |
|---|---|---|---|---|---|
| 11 | cyclohexane-tetraol-CH2OH | —O— | —(CH$_2$)$_{24}$CH$_3$ | —CH(OH)— | —(CH$_2$)$_{13}$CH$_3$ |
| 12 | cyclohexane-tetraol-CH2OH | —O— | —(CH$_2$)$_{24}$CH$_3$ | —CH$_2$— | —(CH$_2$)$_{13}$CH$_3$ |
| 13 | cyclohexane-tetraol-CH2OH | —O— | —(CH$_2$)$_{24}$CH$_3$ | —CH=CH— | —(CH$_2$)$_{12}$CH$_3$ |
| 14 | cyclohexane-tetraol-CH2OH | —O— | —(CH$_2$)$_{16}$CH$_3$ | —CH(OH)— | —(CH$_2$)$_{13}$CH$_3$ |
| 15 | cyclohexane-tetraol-CH2OH | —O— | —CH(OH)(CH$_2$)$_{21}$CH$_3$ | —CH(OH)— | —(CH$_2$)$_{13}$CH$_3$ |
| 16 | cyclohexane-tetraol-CH2OH | —NH— | —(CH$_2$)$_{24}$CH$_3$ | —CH(OH)— | —(CH$_2$)$_{13}$CH$_3$ |

TABLE 1-continued $$\text{R}^1-\text{X}-\text{CH}_2-\text{CH}(\text{NHC}(=\text{O})\text{R}^2)-\text{CH}(\text{OH})-\text{Y}-\text{R}^3$$

| compound No. | R¹ | X | R² | Y | R³ |
|---|---|---|---|---|---|
| 17 | cyclohexane with OH, OH, CH₂OH, HO, OH substituents | —NH— | —(CH₂)₂₄CH₃ | —CH₂— | —(CH₂)₁₂CH₃ |
| 18 | cyclohexane with OH, OH, CH₂OH, HO, OH substituents | —NH— | —(CH₂)₂₄CH₃ | —CH=CH— | —(CH₂)₁₂CH₃ |
| 19 | cyclohexane with OH, OH, CH₂OH, HO, OH substituents | —O— | —CH(OH)(CH₂)₂₁CH₃ | —CH(OH)— | —(CH₂)₁₁CH(CH₃)₂ |
| 20 | cyclohexane with OH, OH, CH₂OH, HO, OH substituents | —O— | —(CH₂)₂₄CH₃ | —CH(OH)— | —C₆H₄(CH₂)₉CH₃ |

TABLE 2

$$\text{R}^1-\text{X}-\text{CH}_2-\text{CH}(\text{NHC}(=\text{O})\text{R}^2)-\text{CH}(\text{OH})-\text{Y}-\text{R}^3$$

| compound No. | R¹ | X | R² | Y | R³ |
|---|---|---|---|---|---|
| 21 | cyclohexane with OH, OH, CH₂OH, HO, OH substituents | —CH₂— | —(CH₂)₂₄CH₃ | —CH(OH)— | —(CH₂)₁₃CH₃ |
| 22 | cyclohexane with OH, OH, CH₂OH, HO, OH substituents | —CH₂— | —(CH₂)₂₄CH₃ | —CH₂— | —(CH₂)₁₃CH₃ |

TABLE 2-continued $$\text{R}^1-\text{X}-\text{CH}_2-\underset{\underset{\underset{\text{O}}{\|}}{\text{NHC}-\text{R}^2}}{\text{CH}}-\underset{\text{OH}}{\text{CH}}-\text{Y}-\text{R}^3$$

| compound No. | R¹ | X | R² | Y | R³ |
|---|---|---|---|---|---|
| 23 | ![sugar with OH, OH, HO, OH] | —CH₂— | —(CH₂)₂₄CH₃ | —CH=CH— | —(CH₂)₁₂CH₃ |
| 24 | ![sugar with OH, OH, HO, OH] | —O— | —(CH₂)₅C₆H₅ | —CH(OH)— | —(CH₂)₁₃CH₃ |
| 25 | ![sugar with OH, OH, HO, OH] | —S— | —(CH₂)₂₄CH₃ | —CH(OH)— | —(CH₂)₁₃CH₃ |
| 26 | ![sugar with OH, OH, HO, OH] | —S— | —(CH₂)₂₄CH₃ | —CH₂— | —(CH₂)₁₃CH₃ |
| 27 | ![sugar with OH, OH, HO, OH] | —S— | —(CH₂)₂₄CH₃ | —CH=CH— | —(CH₂)₁₂CH₃ |

TABLE 3

$$\text{R}^1-\text{X}-\text{CH}_2-\underset{\underset{\underset{\text{O}}{\|}}{\text{NHC}-\text{R}^2}}{\text{CH}}-\underset{\text{OH}}{\text{CH}}-\text{Y}-\text{R}^3$$

| compound No. | R¹ | X | R² | Y | R³ |
|---|---|---|---|---|---|
| 31 | ![sugar with OH, HO, HO, OH] | —O— | —(CH₂)₂₄CH₃ | —CH(OH)— | —(CH₂)₁₃CH₃ |

TABLE 3-continued

[Structure: R¹–X–CH₂–CH(NHC(=O)R²)–CH(OH)–Y–R³]

| compound No. | R¹ | X | R² | Y | R³ |
|---|---|---|---|---|---|
| 32 | cyclohexane with CH₂OH, OH, HO, HO, OH | —O— | —(CH₂)₂₄CH₃ | —CH₂— | —(CH₂)₁₃CH₃ |
| 33 | cyclohexane with CH₂OH, OH, HO, HO, OH | —O— | —(CH₂)₂₄CH₃ | —CH=CH— | —(CH₂)₁₂CH₃ |
| 34 | cyclohexane with CH₂OH, OH, HO, HO, OH | —O— | —(CH₂)₁₆CH₃ | —CH(OH)— | —(CH₂)₁₃CH₃ |
| 35 | cyclohexane with CH₂OH, OH, HO, HO, OH | —O— | —CH(OH)(CH₂)₂₁CH₃ | —CH(OH)— | —(CH₂)₁₃CH₃ |
| 36 | cyclohexane with CH₂OH, OH, HO, HO, OH | —NH— | —(CH₂)₂₄CH₃ | —CH(OH)— | —(CH₂)₁₃CH₃ |
| 37 | cyclohexane with CH₂OH, OH, HO, HO, OH | —NH— | —(CH₂)₂₄CH₃ | —CH₂— | —(CH₂)₁₂CH₃ |
| 38 | cyclohexane with CH₂OH, OH, HO, HO, OH | —NH— | —(CH₂)₂₄CH₃ | —CH=CH— | —(CH₂)₁₂CH₃ |
| 39 | cyclohexane with CH₂OH, OH, HO, HO, OH | —O— | —CH(OH)(CH₂)₂₁CH₃ | —CH(OH)— | —(CH₂)₁₁CH(CH₃)₂ |

TABLE 3-continued structure:

$$R^1\text{—}X\text{—}CH_2\text{—}CH(NHC(O)R^2)\text{—}CH(OH)\text{—}Y\text{—}R^3$$

| compound No. | R¹ | X | R² | Y | R³ |
|---|---|---|---|---|---|
| 40 | cyclohexane(CH₂OH)(OH)₃ | —O— | —(CH₂)₂₄CH₃ | —CH(OH)— | —C₆H₄(CH₂)₉CH₃ |

TABLE 4 structure:

$$R^1\text{—}X\text{—}CH_2\text{—}CH(NHC(O)R^2)\text{—}CH(OH)\text{—}Y\text{—}R^3$$

| compound No. | R¹ | X | R² | Y | R³ |
|---|---|---|---|---|---|
| 41 | cyclohexane(CH₂OH)(OH)₃ | —CH₂— | —(CH₂)₂₄CH₃ | —CH(OH)— | —(CH₂)₁₃CH₃ |
| 42 | cyclohexane(CH₂OH)(OH)₃ | —CH₂— | —(CH₂)₂₄CH₃ | —CH₂— | —(CH₂)₁₃CH₃ |
| 43 | cyclohexane(CH₂OH)(OH)₃ | —CH₂— | —(CH₂)₂₄CH₃ | —CH═CH— | —(CH₂)₁₂CH₃ |
| 44 | cyclohexane(CH₂OH)(OH)₃ | —O— | —(CH₂)₅C₆H₅ | —CH(OH)— | —(CH₂)₁₃CH₃ |
| 45 | cyclohexane(CH₂OH)(OH)₃ | —S— | —(CH₂)₂₄CH₃ | —CH(OH)— | —(CH₂)₁₃CH₃ |

TABLE 4-continued

![structure: R¹-X-CH₂-CH(NHC(O)-R²)-CH(OH)-Y-R³]

| compound No. | R¹ | X | R² | Y | R³ |
|---|---|---|---|---|---|
| 46 | (5a-carba sugar with OH, HO, HO, OH) | —S— | —(CH$_2$)$_{24}$CH$_3$ | —CH$_2$— | —(CH$_2$)$_{13}$CH$_3$ |
| 47 | (5a-carba sugar with OH, HO, HO, OH) | —S— | —(CH$_2$)$_{24}$CH$_3$ | —CH=CH— | —(CH$_2$)$_{12}$CH$_3$ |

TABLE 5

![structure: R¹-X-CH₂-CH(NHC(O)-R²)-CH(OH)-Y-R³]

| compound No. | R¹ | X | R² | Y | R³ |
|---|---|---|---|---|---|
| 51 | (5a-carba sugar with HO, HO, HO) | —O— | —(CH$_2$)$_{24}$CH$_3$ | —CH(OH)— | —(CH$_2$)$_{13}$CH$_3$ |

Of these, particularly preferable compound includes the following compounds.

[1] (2S,3S,4R)-1-(5a-carba-α-D-galactopyranosyloxy)-2-(hexacosanoylamino)-3,4-octadecanediol (compound 11')
[2] (2S,3S,4R)-1-(5a-carba-α-D-galactopyranosylthio)-2-(hexacosanoylamino)-3,4-octadecanediol (compound 25')
[3] (2S,3S,4R)-1-(5a-carba-α-D-glucopyranosyloxy)-2-(hexacosanoylamino)-3,4-octadecanediol (compound 31')
[4] (2S,3S,4R)-1-(5a-carba-α-D-glucopyranosylthio)-2-(hexacosanoylamino)-3,4-octadecanediol (compound 45')
[5] (2S,3S,4R)-1-(5a-carba-α-D-fucopyranosyloxy)-2-(hexacosanoylamino)-3,4-octadecanediol (compound 51')

Specific examples of preferable compound (2) in the present invention include, but are not limited to, compounds (2-1), (2-2), (2-3) and (2-4) described in Examples.

Now, preferable embodiments of the production methods of compounds (1) and (2) of the present invention are explained. The compounds of the present invention can be produced by various methods and, for example, they can be produced according to the method described in the following Scheme 1 or a method analogous thereto. In the Scheme, A is a hydroxyl-protecting group, and other symbols are as defined above. Examples of the hydroxyl-protecting group for A include those similar to the hydroxyl-protecting group for the aforementioned A¹. The following compound (2') and compound (2") are encompassed in compound (2) of the present invention.

The starting compound (A) can be prepared, for example, according to the method described in Tetrahedron Letters, 2007, 48, 3343-3347 or a method analogous thereto. The starting compound (B) can be prepared, for example, according to the method described in The Journal of Organic Chemistry, 2004, 69, 7694-7699 or a method analogous thereto.

<Scheme 1>

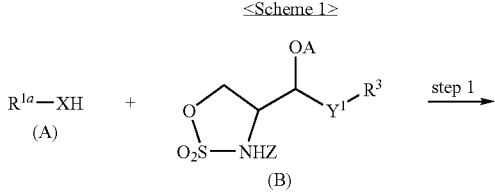

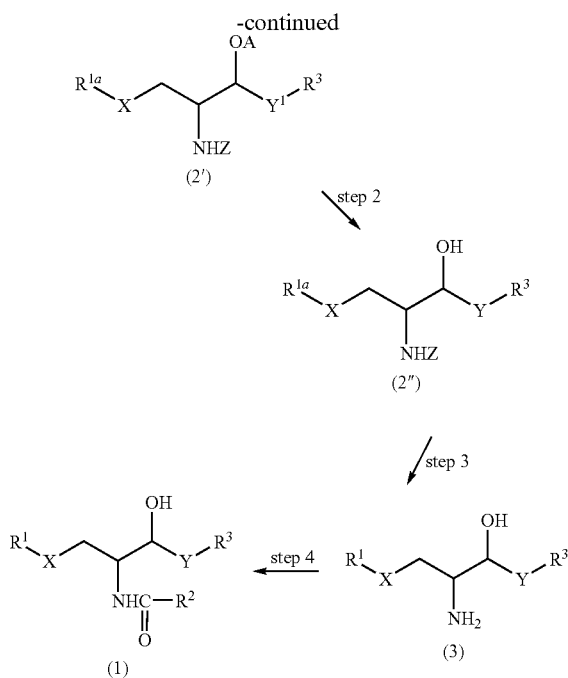

(Step 1)

In step 1, compound (A) is reacted with compound (B) in the presence of a base to give compound (2'). The order of addition of the reagents is not particularly limited. For example, compound (A) is dissolved in a solvent, and compound B solution is added to allow reaction in the presence of a base. In this case, it is preferable to add reagents at −20° C.—room temperature and, after the addition, the reaction is matured by heating at about 50-100° C. The reaction time can be appropriately set according to the reagents to be used. It is generally 1-48 hr, preferably 10-20 hr. The amount of compound (A) to be used is generally 0.2-2 equivalents, preferably 0.5-1 equivalent, relative to compound (B).

Examples of the base include alkali metal hydride (e.g., sodium hydride, potassium hydride), alkali metal alkoxide (e.g., sodium methoxide, potassium methoxide, sodium ethoxide, potassium ethoxide, sodium propoxide, potassium propoxide, sodium 2-propoxide, potassium 2-propoxide), strongly basic organic amine (e.g., 1,8-diazabicyclo[5.4.0]undec-7-ene (DBU), 1,5-diazabicyclo[4.3.0]non-5-ene (DBN)), organic amine alkali metal salt (e.g., lithium bis(trimethylsilyl)amide, sodium bis(trimethylsilyl)amide, potassium bis(trimethylsilyl)amide, lithium diisopropylamide), strongly basic alkyl alkali metal salt (e.g., methyllithium, butyllithium). Of these, sodium hydride or sodium bis(trimethylsilyl)amide is preferably used. The amount of the base to be used is generally 1-5 equivalents, preferably 1-3 equivalents, relative to compound (A).

Examples of the solvent include nonprotonic solvents such as N,N-dimethylformamide, ethers (e.g., diethyl ether, tetrahydrofuran) and the like. These may be used in a mixture of two or more kinds thereof. The amount of the solvent to be used is generally 10- to 100-fold volume, preferably 20- to 50-fold volume, relative to compound (A).

After completion of the reaction, the reaction mixture is concentrated, a solvent (e.g., ether) is added to the residue, and acid (e.g., aqueous sulfuric acid solution) is added under cooling. Then, the solution is neutralized with a base (e.g., sodium carbonate), and partitioned. The organic layer is washed with saturated brine etc. and dried over anhydrous magnesium sulfate etc. The solution is filtered, the filtrate is concentrated under reduced pressure, and the residue is purified by column chromatography to give compound (2').

(Step 2)

In step 2, protecting group A is removed from —OA of compound (2') to give compound (2″). Depending on the kind of the amino-protecting group, deprotection thereof at this stage is also possible. The method for removal is selected according to the kind of the protecting group. For example, compound (2') is reacted with acid in a solvent.

As acid, a strong acid such as trifluoroacetic acid, p-toluenesulfonic acid, hydrochloric acid and the like is preferably used. The amount of the acid to be used is generally a catalytic amount to 10-fold equivalents, preferably 1- to 2-fold equivalents, relative to compound (2').

The reaction temperature is generally 0° C.—heating under reflux temperature, preferably room temperature—heating under reflux temperature, and the reaction time is generally 2-12 hr, preferably 2-4 hr.

Examples of the solvent include lower alcohols (e.g., methanol, ethanol), halogenated hydrocarbons (e.g., dichloromethane, chloroform) and ethers (e.g., diethyl ether, tetrahydrofuran), which may be used in a mixture. The amount of the solvent to be used is generally 5- to 100-fold volume, preferably 10- to 50-fold volume, relative to compound (2').

After completion of the reaction, the reaction mixture is concentrated and the residue is diluted with a solvent (e.g., esters such as ethyl acetate and the like). Then, the solution is neutralized with a basic aqueous solution (e.g., aqueous sodium hydrogen carbonate solution), and partitioned. The organic layer is washed with saturated brine etc. and dried over anhydrous magnesium sulfate etc. The solution is filtered, the filtrate is concentrated under reduced pressure, and the residue is purified by column chromatography to give compound (2″).

(Step 3)

In step 3, the carbasugar moiety of the hydroxyl-protecting group and amino-protecting group are removed from compound (2″) to give compound (3). In this step, for example, compound (2″) is reacted in a solvent in the presence of an acid and a reduction catalyst.

As the solvent, a mixed solvent of alcohol solvent and a halogen solvent is preferable, and a mixed solvent of methanol and chloroform is more preferable. The amount of the solvent to be used is generally 10- to 50-fold volume, preferably 10- to 20-fold volume, relative to compound (2″).

Examples of the reduction catalyst include palladium-C, palladium hydroxide, platinum oxide, Raney-nickel and the like. The amount of the reduction catalyst to be used only needs to be a catalytic amount relative to compound (2″).

Examples of the acid include hydrochloric acid, acetic acid, trifluoroacetic acid, p-toluenesulfonic acid and the like. The amount of the acid to be used is generally catalytic amount—10 equivalents, preferably 1-2 equivalents, relative to compound (2″).

The reaction time is generally 1-24 hr, preferably 12-24 hr. The reaction temperature is generally 0° C.—heating under reflux temperature, preferably room temperature—heating under reflux temperature.

After completion of the reaction, the reaction mixture is filtered, the filtrate is concentrated under reduced pressure, and the residue is purified by column chromatography to give compound (3). In this step, the reaction mixture may be filtered, the filtrate may be concentrated and the next step may be performed, without isolation and purification of compound (3).

(Step 4)

In step 4, compound (3) is reacted with acyl halide to give compound (1). Specifically, compound (3) is reacted with acyl halide (e.g., $R^2$—$COX'$ wherein $R^2$ is as defined above, and $X'$ is, for example, a chlorine atom) in a solvent in the presence of a base. The amount of acyl halide to be used is generally 1-2 equivalents, preferably 1-1.2 equivalents, relative to compound (3).

While the solvent is not particularly limited as long as the reaction is not inhibited, it is preferably, for example, a mixed solvent of an alcohol solvent and a halogen solvent (for example, mixed solvent of methanol and chloroform). The amount of the solvent to be used is generally 1- to 20-fold volume, preferably 5- to 10-fold volume, relative to compound (3).

Examples of the base include 4-(N,N-dimethylamino)pyridine and triethylamine, and triethylamine is preferable. The amount of the base to be used is generally 1-5 equivalents, preferably 2-3 equivalents, relative to compound (3).

The reaction temperature is generally 0° C.—heating under reflux temperature, preferably 0° C.—room temperature and the reaction time is generally 10 min-48 hr, preferably 10-20 hr.

After completion of the reaction, the reaction mixture is concentrated, the residue is washed with a mixed solvent of water and methanol, and purified by column chromatography to give compound (1) in a high yield.

As compound (A), selection of an α-configuration or a β-configuration enables production of each object isomer.

Compound (1) wherein X is —$CH_2$— can be produced by, for example, synthesizing $R^{1a}$—$CH_2$-M wherein M is alkali metal from $R^{1a}$—OH according to the method described in Carbohydrate Research 2000, 329, 7-16, and reacting same instead of compound (A) with compound (B) and following Scheme 1.

Compound (1) and compound (2) of the present invention obtained as mentioned above can be converted to an object salt by a method known per se or a method analogous thereto.

Next, the pharmaceutical use of the present invention is explained.

By administration of compound (1) or a salt thereof of the present invention, a complex with the CD1d protein possessed by APC is formed, and the complex is presented to NKT cells. The NKT cells recognizes the complex via TCR, and can selectively produce IFN-γ, which is one kind of cytokine that activates the function of immunocytes, in a large amount, from among the immunoregulatory functions it has, while inhibiting the production of IL-4. To be specific, the IFN-γ/IL-4 ratio was not less than 5, and extremely high selective IFN-γ production was confirmed as compared to conventionally known glycolipids (see FIGS. 1 and 2). Therefore, compound (1) or a salt thereof of the present invention is useful as an anti-cancer agent or an immunostimulator for inhibiting tumor growth, and further for the treatment of a cell proliferation disorder or for correction of Th1/Th2 immunity balance.

Examples of the cancer treatment target include, but are not limited to, carcinomas of esophagus, stomach, kidney, liver, pancreas, breast, colon, kidney, lung (including small cell lung cancer, non-small cell lung cancer), gall bladder, ovary, testis, bladder, cervical division, thyroid gland, prostate and skin (including squamous cell cancer); hematopoietic neoplasm of the lymphoid system (including leukemia, acute lymphatic leukemia, acute lymphoblastic leukemia, B cell lymphoma, T cell lymphoma, Hodgkin lymphoma, non-Hodgkin lymphoma, hairy cell leukemia, Burkitt's lymphoma); hematopoietic neoplasm of the myeloid system (including acute and chronic myelocytic leukemia, myelodysplastic syndrome and acute promyelocytic leukemia); tumors of mesenchymal origin (including fibrosarcoma and rhabdomyosarcoma); tumor in the central nervous system and the peripheral nervous system (including astrocytoma, neuroblastoma, glioma and neurinoma); other tumors (including melanoma, seminoma, teratocarcinoma, osteosarcoma, xeroderma pigmentosum, keratoacanthoma, follicular cancer of the thyroid, Kaposi's sarcoma).

The cell proliferation disorder is a concept including familial adenomatous polyposis, psoriasis, benign prostatic hyperplasia, neurofibromatosis, vascular smooth muscle cell proliferation relating to atherosclerosis, pulmonary fibrosis, arthritis, glomerulonephritis, postoperative stenosis and restenosis.

In addition, compound (1) or a salt thereof of the present invention shows very high stability in the body as compared to α-GalCer, and activates NKT cells even when a trace amount thereof is administered. Although the reason for such effect is not entirely clear, the present inventors assume that the effect is provided by the enhanced galactosidase resistance due to the pseudocarbohydrate wherein the ring oxygen atom of sugar is replaced with a methylene group, which is possessed by compound (1) of the present invention as a skeleton.

As the subject of administration of compound (1) or a salt thereof of the present invention, mammals such as human and the like, and the like can be mentioned.

When compound (1) or a salt thereof of the present invention is administered to human, it can be safely administered orally or parenterally as it is or in the form of a pharmaceutical composition such as an agent for oral administration (e.g., powder, granule, tablet, capsule), an agent for parenteral administration (e.g., injection, suppository (e.g., rectal suppository, vaginal suppository)) and the like, which is obtained by mixing compound (1) or a salt thereof with a pharmacologically acceptable carrier (e.g., excipient, diluent) and the like. These preparations can be produced by a conventionally known method.

Examples of the injection include subcutaneous injection, intravenous injection, intramuscular injection, intraperitoneal injection, drip infusion and the like. Injections can also be prepared into an aqueous injection using compound (1) or a salt thereof together with a solubilizer (e.g., β-cyclodextrins), dispersing agent (e.g., carboxymethylcellulose, sodium alginate), preservative (e.g., methylparaben, propylparaben, benzyl alcohol, chlorobutanol), isotonicity agent (e.g., sodium chloride, glycerol, sorbitol, glucose) and the like according to a conventional method. It is also possible to prepare an oily injection by dissolving, suspending or emulsifying in vegetable oil (e.g., olive oil, sesame oil, peanut oil, cottonseed oil, corn oil), propylene glycol and the like.

An agent for oral administration can also be produced by appropriately adding, for example, excipient (e.g., lactose, sucrose, starch), disintegrant (e.g., starch, calcium carbonate), binder (e.g., starch, gum arabic, carboxymethylcellulose, polyvinylpyrrolidone, hydroxypropylcellulose), lubricant (e.g., talc, magnesium stearate, polyethylene glycol) and the like to compound (1) or a salt thereof, compression molding the mixture, and coating the resulting product with hydroxypropylmethylcellulose and the like as necessary. Suppository can be produced by mixing compound (1) or a salt thereof and nonirritating excipient (e.g., polyethylene glycol, glyceride of higher fatty acid).

While the daily dose of compound (1) or a salt thereof varies depending on the age, body weight, symptom, dosage form, administration method, dosing period and the like, it is, for example, generally 0.1-1 mg/kg body weight, preferably 0.5-1 mg/kg body weight, more preferably 0.8-1 mg/kg body weight, per patient (adult, body weight about 60 kg), which can be orally or parenterally administered in one to several portions a day.

The present invention also relates to a commercial package comprising a (pharmaceutical) composition comprising compound (1) or a salt thereof, and a written matter describing that the composition can or should be used for immunostimulation, selective IFN-γ production induction or cancer treatment.

EXAMPLES

The present invention is explained in more detail in the following by referring to Examples, which are not to be construed as limitative.

Example 1

(1) Synthesis of Compound 2-1

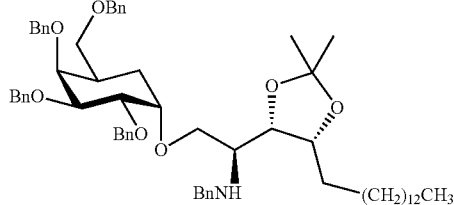
(2-1)

To a mixed solution (2:1, 15 mL) of compound (A1) (440 mg, 0.817 mmol) in N,N-dimethylformamide and tetrahydrofuran was added sodium hydride (60% in mineral oil suspension, 107 mg, 2.68 mmol) under ice-cooling. The mixture was stirred for 25 min under ice-cooling, and a solution of compound (B1) (621 mg, 1.22 mmol) in tetrahydrofuran (5 mL) was added. The reaction mixture was stirred overnight at 80° C. To the reaction solution were further added sodium hydride (60% in mineral oil suspension, 105 mg, 2.63 mmol) and a solution of compound (B1) (539 mg, 1.06 mmol) in tetrahydrofuran (5 mL). The mixture was further stirred for 5 hr at 80° C., cooled to room temperature, and concentrated under reduced pressure to mostly evaporate the solvent. To the residue was added diethyl ether (20 mL), and 20% aqueous sulfuric acid solution (20 mL) was added under ice-cooling. The mixture was stirred for 15 min, and neutralized with sodium carbonate (about 8 g). The mixture was stirred for 40 min under ice-cooling, and diluted with ethyl acetate. The organic layer was washed with water, saturated aqueous sodium hydrogen carbonate solution and saturated brine, and dried over anhydrous magnesium sulfate. After filtration, the filtrate was concentrated under reduced pressure to evaporate the solvent. The residue was purified by silica gel column chromatography (20 g, hexane-ethyl acetate=8:1) to give compound (2-1) (599 mg, 76%) as a pale-yellow oil.

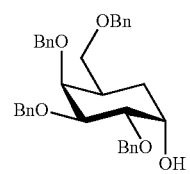
(A1)

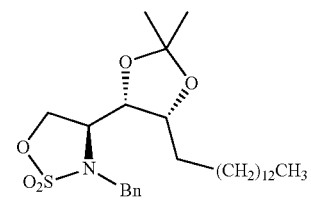
(B1)

$n_D^{21}$=1.5177
$[\alpha]_D^{22}$=+40.6 (c=1.73, CHCl$_3$)
IR (film): $\nu_{max}$=3320 (w, NH), 1605 (w, arom.), 1585 (w, arom.), 1495 (m, arom.), 1095 (br.s, C—O), 735 (s, arom.), 695 (s, arom.) cm$^{-1}$
$^1$H NMR (400 MHz, CDCl$_3$, 25° C.): δ=7.35-7.20 (m, 25H, Ph×2), 4.98 (d, J=12 Hz, 1H, PhCH), 4.77 (d, J=12 Hz, 1H, PhCH), 4.73 (d, J=12 Hz, 1H, PhCH), 4.70 (d, J=12 Hz, 1H, PhCH), 4.69 (d, J=12 Hz, 1H, PhCH), 4.50 (d, J=12 Hz, 1H, PhCH), 4.43 (s, 2H, PhCH×2), 4.12 (br s, 1H, 4'-H), 4.12-4.03 (m, 2H, 2'-, 3-H), 3.93-3.82 (m, 4H, 1'-, 3'-, 4-H, 1-H$_a$, PhCH$_a$N), 3.72-3.67 (m, 1H, 1-H$_b$), 3.68 (d, J=13 Hz, 1H, PhCH$_b$N), 3.51 (t, J=8.8 Hz, 1H, 6'-H$_a$), 3.32-3.28 (m, 1H, 6'-H$_b$), 2.76 (ddd, J=8.4, 4.0, 3.6 Hz, 1H, 2-H), 2.22-2.13 (m, 1H, 5'-H), 1.74-1.23 (m, 28 H, 5a'-, 5-, 6-, 7-, 8-, 9-, 10-, 11-, 12-, 13-, 14-, 15-, 16-, 17-H$_2$), 1.38 (s, 3H, CCH$_3$), 1.27 (s, s, 3H, CCH$_3$), 0.88 (t, J=6.8 Hz, 3H, 18-H$_3$) ppm
$^{13}$C NMR (100 MHz, CDCl$_3$, 25° C.): δ=140.8, 139.6, 139.3, 138.4, 128.4, 128.3, 128.22, 128.17, 128.11, 127.7, 127.63, 127.58, 127.4, 127.3, 127.2, 127.1, 126.8, 107.3, 81.3, 80.1, 78.3, 76.2, 75.7, 74.5, 73.15, 73.12, 72.4, 70.8, 68.2, 56.5, 51.2, 35.8, 31.9, 29.71, 29.66, 29.61, 29.5, 29.3, 28.3, 26.6, 26.2, 25.9, 22.7, 14.1 ppm (2) Synthesis of compound 2-2

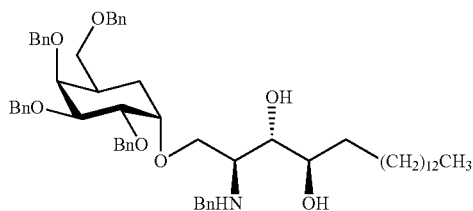
(2-2)

To a mixed solution (1:1, 40 mL) of compound (2-1) (515 mg, 0.532 mmol) in methanol and dichloromethane was added p-toluenesulfonic acid monohydrate (165 mg, 0.867 mmol), and the mixture was stirred for 10 hr with heating under reflux. The mixture was cooled to room temperature and concentrated under reduced pressure to evaporate the solvent. The residue was diluted with ethyl acetate, and neutralized with saturated aqueous sodium hydrogen carbonate solution. The organic layer was washed with saturated aqueous sodium hydrogen carbonate solution and saturated brine, and dried over anhydrous magnesium sulfate. After filtration, the filtrate was concentrated under reduced pressure to evaporate the solvent. The residue was purified by silica gel column chromatography (20 g, chloroform-methanol=100:1) to give compound (2-2) (481 mg, 97%) as colorless needle crystals.

mp=44.5-47.0° C.

$[\alpha]_D^{23}$=+31.0 (c=1.40, CHCl$_3$)

IR (KBr): $\nu_{max}$=3450 (br.s, OH), 3340 (w, NH), 1605 (w, arom.), 1585 (w, arom.), 1495 (s, arom.), 1095 (br.s, C—O), 745 (s, arom.), 695 (s, arom.) cm$^{-1}$ $^1$H NMR (400 MHz, CDCl$_3$, 25° C.): δ=7.22-7.39 (m, 25 H, Ph×5), 4.95 (d, J=11 Hz, 1H, PhCH), 4.84 (d, J=12 Hz, 1H, PhCH), 4.75 (s, 2H, PhCH×2), 4.69 (d, J=12 Hz, 1H, PhCH), 4.47 (d, J=11 Hz, 1H, PhCH), 4.42 (s, 2H, PhCH×2), 4.09 (br s, 1H, 4'-H), 3.94-3.89 (m, 2H, 1-H$_b$, 2'-H), 3.84 (d, J=13 Hz, 1H, PhCH$_a$N), 3.72 (d, J=13 Hz, 1H, PhCH$_b$N), 3.78-3.74 (m, 2H, 1-H$_b$, 3'-H), 3.68-3.61 (m, 2H, 1'-, 4'-H), 3.46 (t, J=8.8 Hz, 1H, 6'-H$_a$), 3.38 (t, J=8.0 Hz, 1H, 3-H), 3.26 (dd, J=8.8, 5.6 Hz, 1H, 6'-H$_b$), 2.80 (br d, J=8.0 Hz, 1H, 2-H), 2.12-2.02 (m, 1H, 5'-H), 1.79-1.69 (m, 1H, 5-H$_b$), 1.57-1.20 (m, 27H, 5-H$_a$, 5a'-, 6-, 7-, 8-, 9-, 10-, 11-, 12-, 13-, 14-, 15-, 16-, 17-H$_2$), 0.88 (t, J=7.2 Hz, 3H, 18-H$_3$) ppm $^{13}$C NMR (100 MHz, CDCl$_3$, 25° C.): δ=139.4, 139.1, 138.7, 138.2, 137.9, 128.5, 128.37, 128.34, 128.24, 128.21, 128.1, 127.8, 127.7, 127.6, 127.43, 127.35, 127.30, 81.7, 79.5, 76.8, 75.7, 75.4, 74.6, 73.8, 73.2, 73.0, 71.2, 70.6, 67.1, 62.1, 51.0, 35.8, 34.7, 31.9, 30.0, 29.81, 29.74, 29.71, 29.65, 29.3, 27.2, 25.2, 22.7, 14.1 ppm (3) Synthesis of Compound 11'

(11')

To a solution of compound (2-2) (249 mg, 0.268 mmol) in methanol (10 mL) were added cyclohexene (2 mL), 1N hydrochloric acid (268 μL, 0.268 mmol) and 10% palladium-activated carbon (100 mg) in this order, and the mixture was stirred with heating under reflux for 6 hr. The mixture was cooled to room temperature, diluted with a chloroform-methanol (5:1) mixed solvent, and filtered through celite to remove palladium-activated carbon catalyst. The filtrate was concentrated under reduced pressure to evaporate the solvent to give a debenzylated intermediate (144 mg, quant.) as a colorless solid.

To a mixed solution (5:1, 30 mL) of the obtained intermediate in chloroform and methanol were added triethylamine (90 μL, 0.65 mmol) and cerotyl chloride (ClCO(CH$_2$)$_{24}$CH$_3$, 117 mg, 0.282 mmol) in this order, and the mixture was stirred for 20 hr at room temperature. The reaction mixture was concentrated under reduced pressure to evaporate the solvent, and the residue was washed with a mixed solution (2:1) of water and methanol, dried under reduced pressure and purified by silica gel column chromatography (20 g, chloroform-methanol=10:1) to give compound 11' (138 mg, 60%) as a colorless powder.

mp=147-149° C.

$[\alpha]_D^{23}$=+27.8 (c=0.32, pyridine)

IR (KBr): $\nu_{max}$=3360 (br.s, OH), 3280 (m, NH), 2960 (m, CH), 2920 (s, CH), 2850 (s, CH), 1640 (br.s, CO), 1545 (br.m, 5NH), 1470 (m, CH$_2$), 1075 (br.m, C—O), 960 (w), 890 (w), 720 (m) cm$^{-1}$ $^1$H NMR (400 MHz, pyridine-d$_5$, 25° C.): δ=8.43 (d, J=8.4 Hz, 1H, NH), 6.85-6.82 (m, 1H, OH), 6.37 (d, J=6.4 Hz, 1H, OH), 6.31-6.28 (m, 1H, OH), 6.07 (d, J=5.2 Hz, 1H, OH), 6.00-5.98 (m, 1H, OH), 5.97 (t, J=5.4 Hz, 1H, OH), 5.21-5.18 (m, 1H, 2-H), 4.69 (br.s, 1H, 4"-H), 4.50 (dd, J=10, 4.0 Hz, 1H, 1-H$_a$) 4.47-4.43 (m, 1H, 2"-H), 4.34-4.18 (m, 5H, 3-, 4-, 1"-, 3"-H, 6"-H$_a$), 4.26 (dd, J=10, 5.2 Hz, 1H, 1-H$_b$), 4.00 (ddd-like, J=9.6, 5.4, 4.8 Hz, 1H, 6"-H$_b$), 2.51-2.42 (m, 1H, 5"-H), 2.44 (t, J=7.6 Hz, 2H, 2'-H$_2$), 2.33-2.24 (m, 1H, 5-H$_a$), 2.14-2.06 (m, 1H, 5a"-H$_a$), 2.00 (br.t, J=13 Hz, 1H, 5a"-H$_b$), 1.98-1.84 (m, 2H, 5-H$_b$, 6-H$_a$), 1.82 (quint.-like, J=7.6 Hz, 2H, 3'-H$_2$), 1.76-1.67 (m, 1H, 6-H$_b$), 1.50-1.17 (m, 66H, 7-, 8-, 9-, 10-, 11-, 12-, 13-, 14-, 15-, 16-, 17-, 4'-, 5'-, 6'-, 7'-, 8'-, 9'-, 10'-, 11'-, 12'-, 13'-, 14'-, 15'-, 16'-, 17'-, 18'-, 19'-, 20'-, 21'-, 22'-, 23'-, 24'-, 25'-H$_2$), 0.85 (t, J=7.2 Hz, 6H, 18-, 26'-H$_3$) ppm $^{13}$C NMR (100 MHz, CDCl$_3$, 25° C.): δ=173.1, 80.2, 76.6, 73.6, 72.8, 72.6, 71.5, 70.6, 64.2, 51.5, 38.6, 36.8, 34.2, 32.1, 30.4, 30.2, 30.04, 30.00, 29.94, 29.89, 29.83, 29.7, 29.6, 26.6, 26.4, 22.9, 14.3 ppm Example 2

Synthesis of Compound 51'

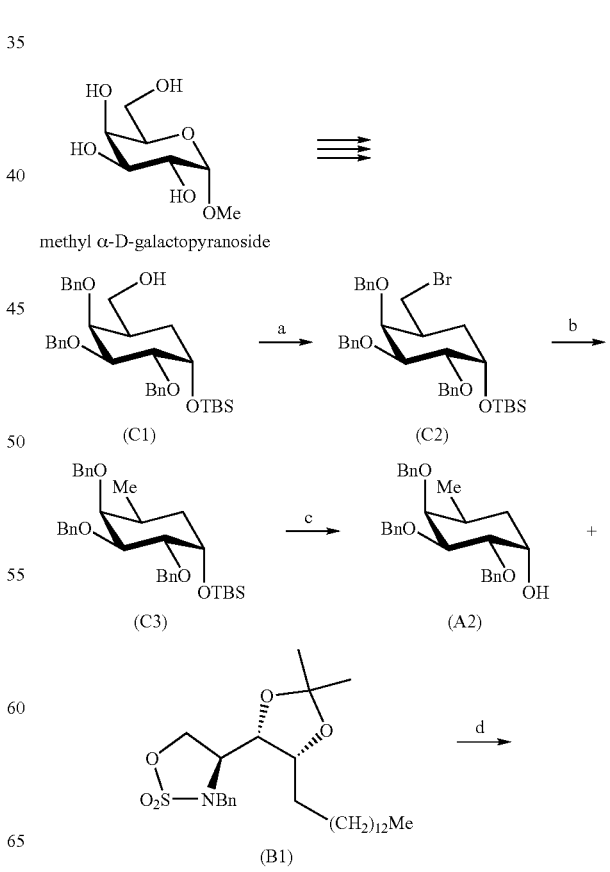

-continued

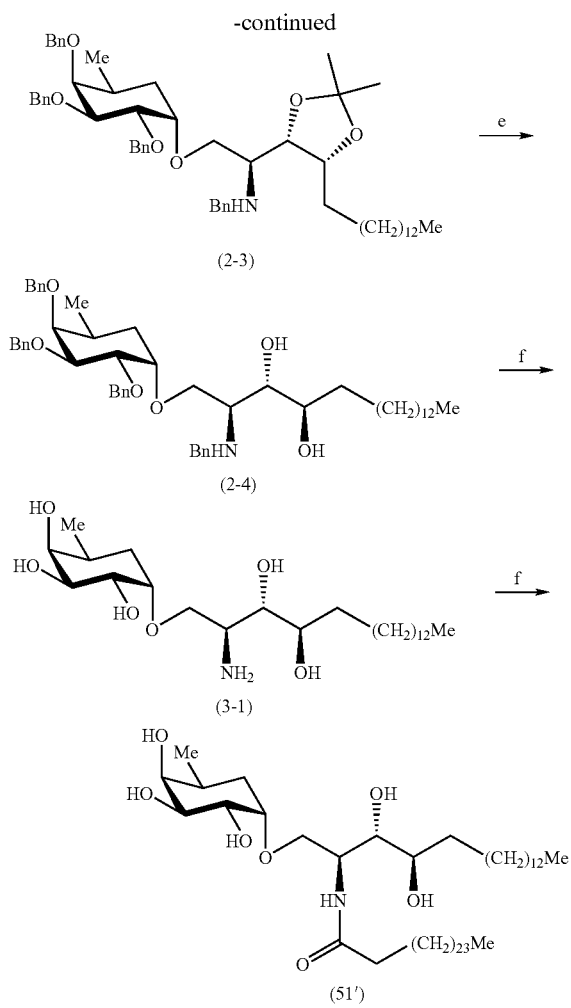

(Step a)

Compound (C1) was prepared according to the method described in Tetrahedron Letters, 2007, 48, 3343-3347.

To a solution of compound (C1) (221 mg, 0.393 mmol) in pyridine (2 mL) were added triphenylphosphine (268 mg, 1.02 mmol) and carbon tetrabromide (437 mg, 1.32 mmol). The mixture was stirred for 15 hr at 65° C., allowed to cool to room temperature, and water was added. The mixture was diluted with ethyl acetate, and the organic layer was washed with water, saturated copper sulfate aqueous solution, water, saturated aqueous sodium hydrogen carbonate solution and saturated brine in this order, and dried over anhydrous magnesium sulfate. The reaction mixture was concentrated under reduced pressure to evaporate the solvent, and the residue was purified by silica gel column chromatography (20 g, hexane: ethyl acetate=40:1) to give compound (C2) (150 mg, 61%) as a colorless oil.

(Step b)

To a solution of compound (C2) (150 mg, 0.239 mmol) in dry diethyl ether (5 mL) was added a solution (1.57 M, 0.46 mL, 0.72 mmol) of tert-butyllithium in pentane at −78° C. The mixture was stirred for 1 hr at −78° C., and saturated aqueous ammonium chloride solution was added. The mixture was warmed to room temperature, stirred for 30 min, and diluted with ethyl acetate. The organic layer was washed with water and saturated brine in this order, and dried over anhydrous magnesium sulfate. The solution was concentrated under reduced pressure to evaporate the solvent, and the residue was purified by silica gel column chromatography (10 g, hexane: ethyl acetate=15:1) to give a compound (C3) (104 mg, 79%) as a colorless oil.

(Step c)

To a solution of compound (C3) (104 mg, 0.189 mmol) in tetrahydrofuran (4 mL) was added a solution (1.0 M, 0.58 ml, 0.58 mmol) of tetra-n-butylammonium fluoride in tetrahydrofuran. The mixture was stirred for 3 hr at room temperature, and water was added. The mixture was diluted with ethyl acetate, and the organic layer was washed with water and saturated brine in this order, and dried over anhydrous magnesium sulfate. The solution was concentrated under reduced pressure to evaporate the solvent, and the residue was purified by silica gel column chromatography (20 g, hexane:ethyl acetate=10:1) to give compound (A2) (48 mg, 46%) as a colorless oil.

(Step d)

To compound (A2) (44 mg, 0.10 mmol) in N,N-dimethylformamide-dry tetrahydrofuran (2:1, 3 mL) was added sodium hydride (55% in mineral oil suspension, 20 mg, 0.46 mmol) under ice-cooling. The mixture was stirred for 1 hr under ice-cooling, and a solution of compound (B1) (77 mg, 0.15 mmol) in dry tetrahydrofuran (1 ml) was added. The mixture was stirred for 10 hr at 70° C. and allowed to cool to room temperature. Sodium hydride (55% in mineral oil suspension, 20 mg, 0.46 mmol) and a solution of compound (B1) (78 mg, 0.15 mmol) in dry tetrahydrofuran (1 mL) were added. The reaction mixture was stirred for 10 hr at 70° C., allowed to cool to room temperature, and concentrated under reduced pressure. The residue was diluted with diethyl ether, 20% aqueous sulfuric acid solution (5 mL) was slowly added under ice-cooling and the mixture was stirred for 10 min. The reaction mixture was neutralized with sodium hydrogen carbonate (about 2 g) and water was added. The mixture was diluted with diethyl ether, and the organic layer was washed with water, saturated aqueous sodium hydrogen carbonate solution and saturated brine in this order, and dried over anhydrous magnesium sulfate. The solution was concentrated under reduced pressure to evaporate the solvent, and the residue was purified by silica gel column chromatography (20 g, hexane:ethyl acetate=10:1) to give compound (2-3) (50 mg, 58%) as a colorless oil.

(Step e)

To a solution of compound (2-3) (50 mg, 0.058 mmol) in methanol-dichloromethane (2:1, 7.5 mL) was added p-toluenesulfonic acid monohydrate (34 mg, 0.18 mmol). The mixture was stirred for 18 hr at room temperature, and for 5 hr at 60° C. The reaction mixture was concentrated under reduced pressure to evaporate the solvent, and the residue was diluted with ethyl acetate. The organic layer was neutralized with saturated aqueous sodium hydrogen carbonate solution, washed with water, saturated aqueous sodium hydrogen carbonate solution and saturated brine in this order, and dried over anhydrous potassium carbonate. The solution was concentrated under reduced pressure to evaporate the solvent, and the residue was purified by silica gel column chromatography (10 g, hexane:ethyl acetate=3:2) to give compound (2-4) (29 mg, 61%) as a colorless oil.

(Step f)

To a solution of compound (2-4) (29 mg, 0.035 mmol) in methanol (2.5 mL) were added cyclohexene (0.5 mL), 1N hydrochloric acid (35 μL, 0.035 mmol) and 10% palladium-carbon (21 mg). The mixture was stirred for 6 hr at 85° C., and diluted with chloroform-methanol (5:1). The reaction mixture was filtered and the filtrate was concentrated under reduced pressure to give compound (3-1). Compound (3-1)

was dissolved in chloroform-methanol (5:1, 5 mL), and a solution of triethylamine (15 μL, 0.11 mmol) and cerotyl chloride (15 mg, 0.039 mmol) in dry tetrahydrofuran (2 mL) was added thereto. The reaction mixture was stirred for 19 hr at room temperature, and concentrated under reduced pressure. The residue was washed with water and water-methanol (2:1) in this order, dried and purified by silica gel column chromatography (10 g, chloroform:methanol=25:1) to give compound 51' (6 mg, 19%) as a colorless solid.

$^1$H NMR (400 MHz, pyridine-$d_5$) δ=8.41 (1H, d, J=8.4 Hz), 5.20-5.12 (1H, m), 4.44-4.25 (5H, m), 4.21 (1H, dd, J=10, 5.6 Hz), 4.07 (1H, br. s), 3.82 (1H, s), 2.46 (2H, t, J=7.2 Hz), 2.35-2.25 (1H, m), 2.10-2.03 (1H, m), 1.97-1.12 (73 H, m), 1.00 (3H, d, J=6.8 Hz), 0.85 (3H, t, J=6.8 Hz).

Experimental Example 1

Compound 11' was dissolved in 0.5% saline (manufactured by OTSUKA PHARMACEUTICAL CO., LTD) containing Tween 20 (Bio-Rad) and prepared to a dose of 100 μg/kg body weight, 10 μg/kg body weight or 1 μg/kg body weight C57BL/6 mouse (5 per group), and the compound 11' solution (200 μL) was intraperitoneally injected.

α-GalCer was used as a control substance, and 200 μL of each α-GalCer solution prepared to a dose of 100 μg/kg body weight, 10 μg/kg body weight or 1 μg/kg body weight according to a similar method was intraperitoneally injected.

Figure 2:
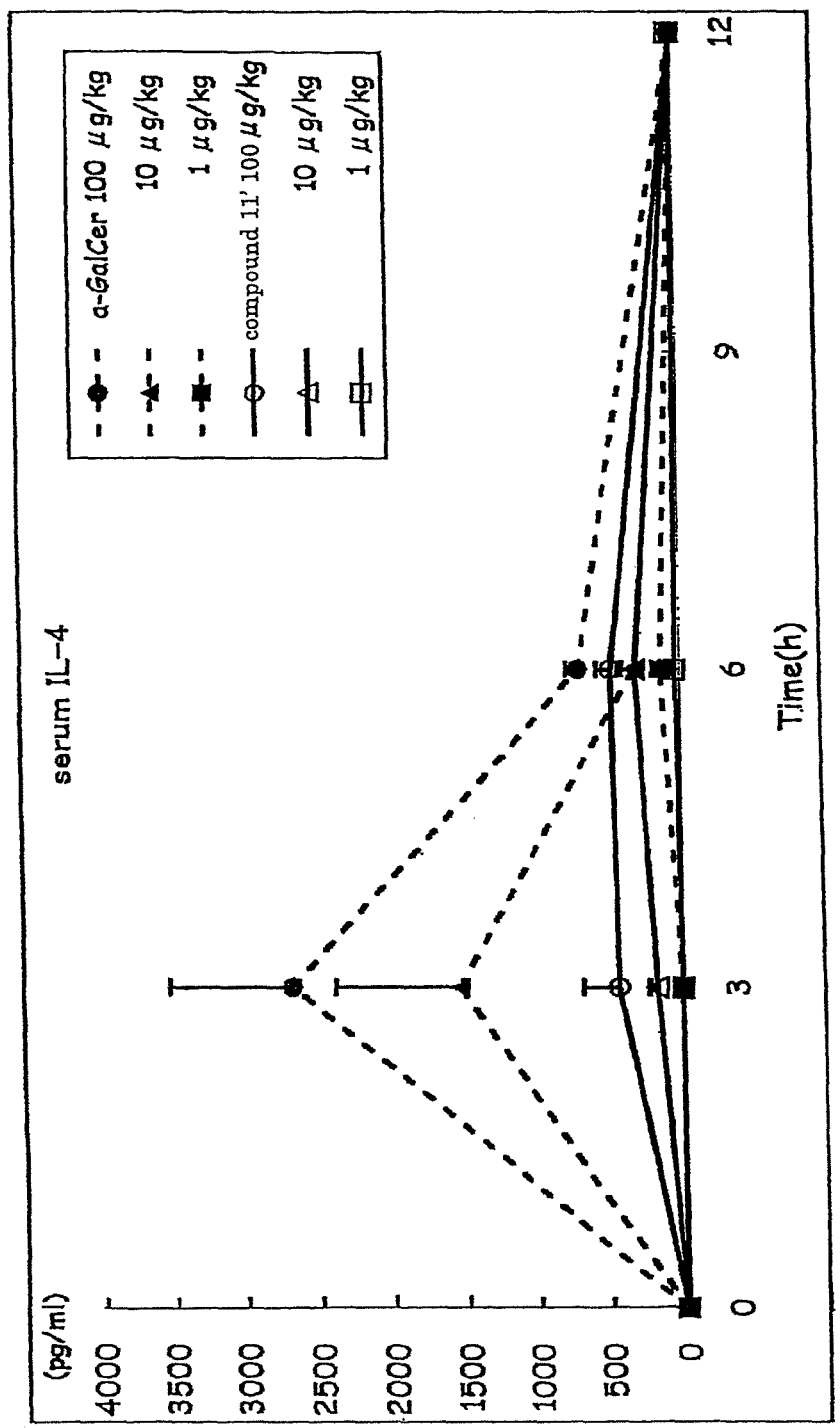
FIG. 2 shows the measurement results of IL-4 production amount in Experimental Example 1. In the figure, μg/kg shows μg/kg body weight.

A group administered with a medium (200 μL of saline containing 0.5% Tween 20) was taken as a negative control. The blood (80 μL) was taken from the orbital plexus venosus immediately before administration and 3, 6, 12, 24, 36 and 48 hr after administration, and the plasma was prepared. The IL-4 content of plasma immediately before administration and 3, 6 and 12 hr after administration, as well as IFN-γ content of plasma immediately before administration and 6, 12, 24, 36 and 48 hr after administration were measured by Cytometric bead array system (BD Biosciences), which is one kind of the ELISA method. The measurement results of IFN-γ production amount are shown FIG. 1 and the measurement results of IL-4 production amount are shown in FIG. 2.

From the above-mentioned results, α-GalCer produced both IFN-γ and IL-4 in large amounts, whereas compound 11' of the present invention preferentially produced IFN-γ but produced IL-4 in a small amount. Since promotion of immunostimulatory action by the administration of compound 11' was confirmed, its effectiveness as an anti-cancer agent and the like has been suggested.

Experimental Example 2

The following experiment was performed for the anti-liver metastasis effect.

The left side of mouse was opened under anesthesia, and the spleen was exposed. 1×10⁶ B16 melanoma was intrasplenically transferred using a 1 mL syringe (TERUMO CORPORATION), maintained for 30 sec, and the blood vessel was sutured. The spleen was isolated and the peritoneal membrane was sutured with a surgical thread (No. 4, Alfresa Pharma Corporation), and the outer skin was joined with a surgical clip. After 3 hr from the cell transfer, α-GalCer and compound 11' were administered each in an amount of 2, 0.2 or 0.02 μg per mouse from the tail vein and the survival rate of each group was examined.

Figure 3:
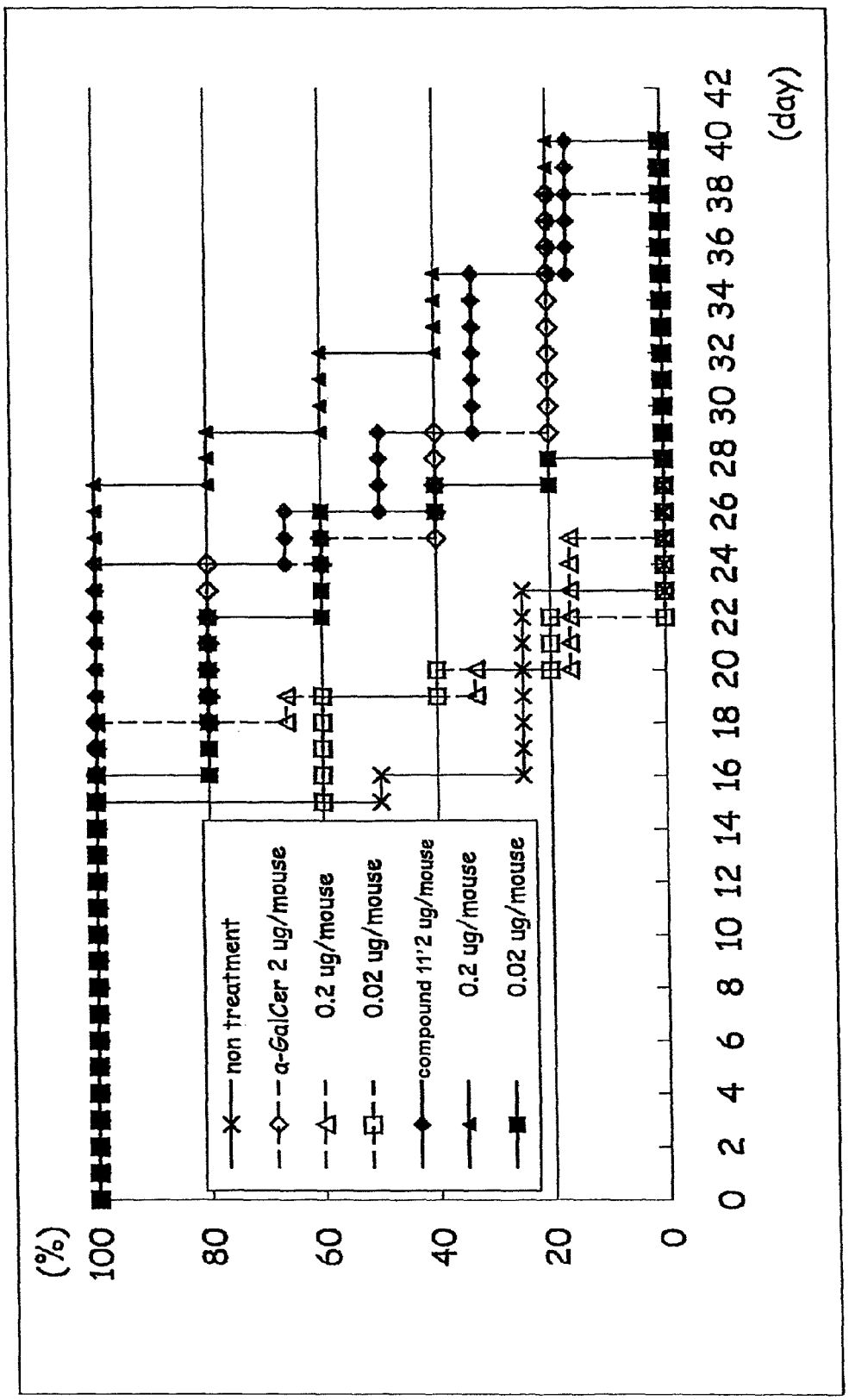
FIG. 3 shows the survival rate in Experimental Example 2.

The results are shown in FIG. 3. The survival period was extended in the compound 11' administration group as compared to the non-treatment group and the α-GalCer administration group. Particularly, administration of 0.2 and 0.02 μg remarkable elongated the survival period of the compound 11' administration group as compared to the α-GalCer administration group.

Experimental Example 3

The following experiment was performed for human NKT cell proliferation and IFN-γ production induction.

Monocytes were prepared from the peripheral blood of a healthy subject by anti-CD14 microbeads (Miltenyi Biotech), and dendritic cells were induced using GM-CSF and IL-4 (Peprotech). To the dendritic cells was added α-GalCer or synthetic glycolipid (α-C-GalCer, compound 11', compound 51'), human peripheral blood mononuclear cell was added and the cells were cultured.

Figure 4:
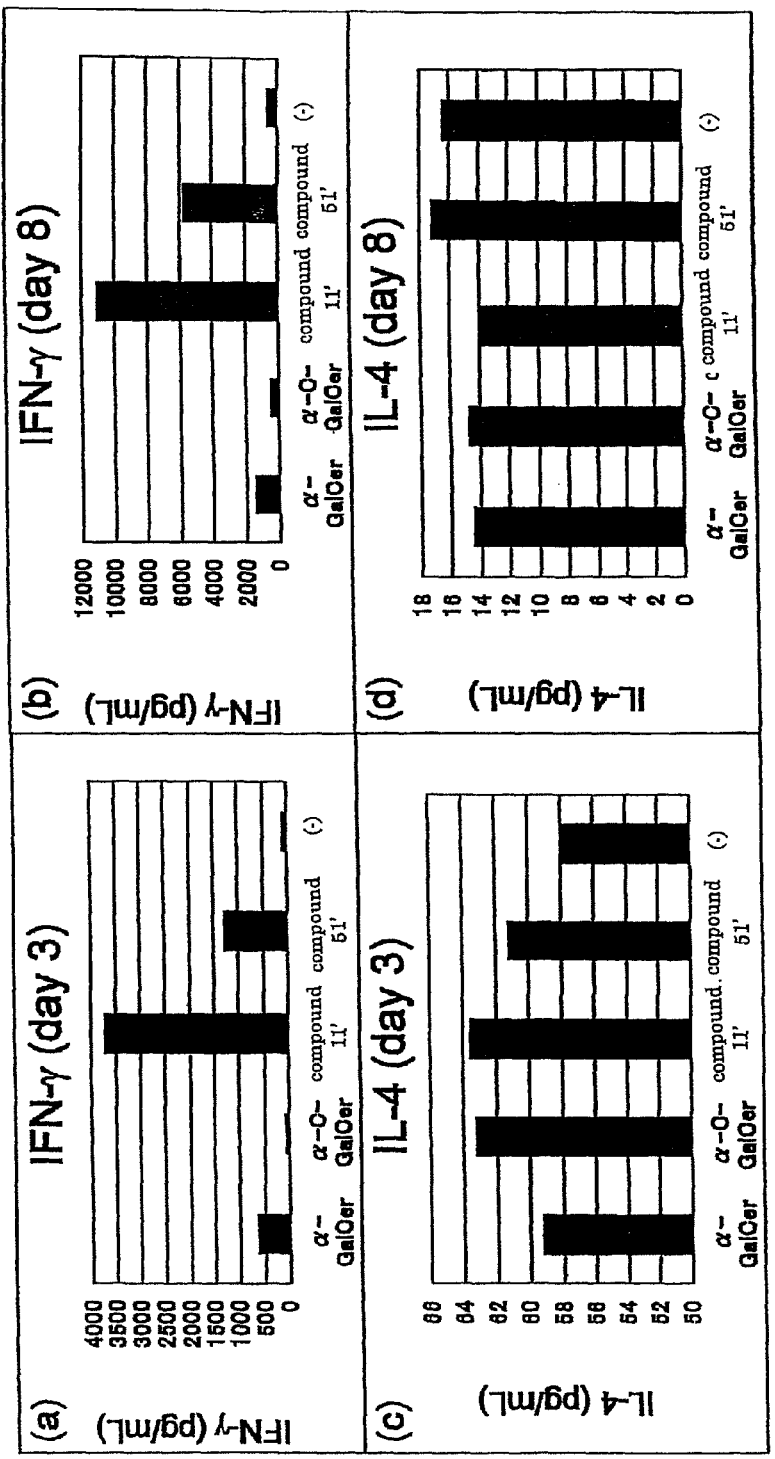
FIG. 4 shows the measurement results of IFN-γ and IL-4 production amounts in Experimental Example 3.

In this experiment, the IFN-γ concentration of the culture supernatants 3 days and 8 days later was measured. As a result, the concentration was very high when stimulated with compound 11' and compound 51' as compared to α-GalCer and α-C-GalCer (FIG. 4 (*a*), (*b*)).

In contrast, IL-4 concentration was almost the same. Therefore, it was shown that compound 11' and compound 51' selectively induced IFN-γ production as compared to α-GalCer and α-C-GalCer (FIG. 4 (*a*)-(*d*)).

This application is based on a patent application No. 2007-042873 filed in Japan, the contents of which are incorporated in full herein by this reference.

The invention claimed is:

1. A compound represented by the following formula (1)

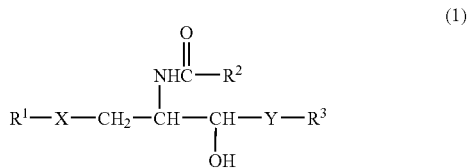

(1)

wherein $R^1$ is a 5a-carba-α-D-galactopyranosyl group, $R^2$ and $R^3$ are each independently a substituted or unsubstituted hydrocarbon group having a carbon number of 1 to 28, X is an oxygen atom, and Y is —CH(OH)—, or a salt thereof.

2. The compound of claim 1, wherein $R^2$ is a substituted or unsubstituted alkyl group having a carbon number of 1 to 28, or a salt thereof.

3. The compound of claim 1, wherein $R^3$ is a substituted or unsubstituted alkyl group having a carbon number of 1 to 28, or a salt thereof.

4. A commercial package comprising a composition comprising a compound represented by the following formula (1)

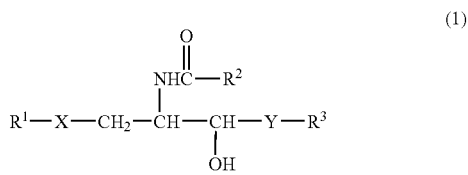

(1)

wherein $R^1$ is a 5a-carba-α-D-galactopyranosyl group, $R^2$ and $R^3$ are each independently a substituted or unsubstituted hydrocarbon group having a carbon number of 1 to 28, X is an oxygen atom, and Y is —CH(OH)—, or a salt thereof, and a written matter describing a method of administration of the composition.

5. The commercial package of claim 4, wherein $R^2$ is a substituted or unsubstituted alkyl group having a carbon number of 1 to 28, and $R^3$ is a substituted or unsubstituted alkyl group having a carbon number of 1 to 28, or a salt thereof.

6. A composition comprising the compound of claim 1 and a pharmacologically acceptable carrier therefor.

* * * * *